United States Patent [19]

Kijima et al.

[11] Patent Number: 5,401,655
[45] Date of Patent: Mar. 28, 1995

[54] PROCESS FOR BIOLOGICALLY PREVENTING DICOTYLEDONOUS PLANT DISEASES USING SYMBIOTICAL BACTERIA

[75] Inventors: Toshio Kijima, Tochigi; Sadao Yonai; Kazuo Oohashi, both of Mibu; Masayuki Amagai, Sano, all of Japan

[73] Assignee: Tochigi Prefecture, Tochigi Prefecture, Japan

[21] Appl. No.: 18,559

[22] Filed: Feb. 17, 1993

Related U.S. Application Data

[63] Continuation-in-part of Ser. No. 849,333, Mar. 10, 1992, abandoned.

[51] Int. Cl.$^6$ .................. C12N 5/00; C12N 5/02; A01N 63/00; A01L 1/00
[52] U.S. Cl. .................. 435/240.45; 435/240.46; 435/822; 435/832; 435/843; 435/847; 435/874; 435/886; 435/910; 47/58; 424/93.1; 424/93.3; 424/93.4; 424/93.43; 424/93.46; 424/93.47
[58] Field of Search .................. 424/93 D, 93 G, 93 E, 424/93 N, 93 B, 93 C; 435/170, 240.45, 240.46, 240.47, 242.45, 822, 832, 843, 847, 874, 886, 910; 71/3, 65; 47/58.17, 58.19, 58.18, 58.26, 58

[56] References Cited

U.S. PATENT DOCUMENTS

| | | | |
|---|---|---|---|
| 2,270,046 | 1/1942 | Grace | 71/3 |
| 4,126,441 | 11/1978 | Williard, Sr. | 71/65 |
| 4,479,936 | 10/1984 | Vandenbergh et al. | 424/93 N |
| 4,569,914 | 2/1986 | Molnar et al. | 47/58.19 |
| 4,663,162 | 5/1987 | Kado et al. | 424/93 K |
| 4,665,031 | 5/1987 | Péron | 47/58.18 |
| 5,061,490 | 10/1991 | Paau et al. | 424/93 D |

FOREIGN PATENT DOCUMENTS

| | | |
|---|---|---|
| 0098234 | 1/1984 | European Pat. Off. . |
| 0302695 | 2/1989 | European Pat. Off. . |
| 0353689 | 2/1990 | European Pat. Off. . |
| 0401560 | 12/1990 | European Pat. Off. . |
| 0408811 | 1/1991 | European Pat. Off. . |
| 0276205 | 2/1990 | Germany . |
| 2099851 | 12/1982 | United Kingdom . |
| 2195656 | 4/1988 | United Kingdom . |
| 1514303 | 10/1989 | U.S.S.R. . |

*Primary Examiner*—Douglas W. Robinson
*Assistant Examiner*—Kristin Larson
*Attorney, Agent, or Firm*—Wenderoth, Lind & Ponack

[57] ABSTRACT

A process for biologically preventing dicotyledonous plant diseases which comprises: cutting a seedling of a dicotyledon which includes the seedling between a cotyledon and less than three leaves at a growth stage; immersing the upper portion of the cut seedling into a symbiotical bacteria suspension having antifungal and antibacterial activities and induced resistance to plant pathogens in order to inoculate the symbiotical bacteria into interior tissues in the vessel and intercellular space of the dicotyledonous plants; cutting the seedlings in a nursery bed or directly planting them in a field for further association of the symbiotical bacteria; and preventing dicotyledonous plant diseases of the dicotyledonous plants.

2 Claims, 2 Drawing Sheets

PROCESS FOR BIOLOGICALLY PREVENTING DICOTYLEDONOUS PLANT DISEASES USING SYMBIOTICAL BACTERIA

This application is a continuation-in-part of Ser. No. 07/849,333, filed Mar. 10, 1992, now abandoned.

BACKGROUND OF THE INVENTION

1. Field of Invention

This invention relates to a process for biologically preventing dicotyledonous plant diseases by cutting a seedling of a dicotyledon, immersing the cut seedlings into asymbiotical bacteria suspension, and cutting the seedlings in a nursery bed or directly planting them in a field.

2. Description of the Prior Art

Recently, vegetables are produced year-round, and they are repeatedly cultivated on the same land. The repeated cultivation of the same vegetables on the same land brings about injury by continuous cropping by soil disease which impedes continuous and safe production of the vegetables.

In order to overcome injury by continuous cropping, it has been proposed to disinfect the soil by chloropicrin or methylbromide, to grow a new type of vegetable having antifungal activity or to cut a seedling into a new type of stock having antifungal activity.

Disinfection of the soil, however, has the environmental drawbacks such that it is not only expensive, but is toxic to men and beasts.

Improvement of a plant having antifungal activity is problematic in that it takes much labor and almost 10 years to grow an improved new plant.

Graft cropping has other problems such that the cost of a seedling and labor of cultivating the new seedling increase unexpectedly so that a new technical method has been needed in the production field.

On the other and, some processes for biologically preventing dicotyledon diseases using antifungal activity have been widely employed.

Certainly, useful bacteria having some antifungal activity to other bacteria can be easily isolated from soil or plants.

When the useful bacteria are put into the soil or spread on the plant as they are, their antifungal activity cannot be exhibited at all because the useful bacteria do not survive in the soil or in the plant.

To this end, a method of stabilizing useful bacteria in the soil by adsorbing the useful bacteria into a carrier and a method of producing useful bacteria which are associated with a plant by improving bacteria have been tried. These method, however, have problems in that they ignore specificity of species, their functions are not exhibited sufficiently, and the growing environment and ecosystem are ignored. As a result, there is not enough of the aforementioned soil disinfection, or growth of a new type of plant having anti-fungal activity, or cutting the new plant into a stock having antifungal activity.

SUMMARY OF THE INVENTION

A principal object of this invention is to provide a process for biologically preventing dicotyledonous plant diseases which comprises the steps of cutting a seedling of dicotyledon at a middle portion of its hypocotyl, immersing the cut seedlings into a symbiotical bacteria suspension having antfungal and antibacterial activities and induced resistance to plant pathogens in order to inoculate the symbiotical bacteria in the interior tissues of the dicotyledonous plant, and cutting the seedlings in a nursery bed or directly planting them in a field for further association of the symbiotical bacteria and preventing the dicotyledonous diseases of the dicotyledon plant.

Another object of this invention is to provide a process for biologically preventing dicotyledon plant diseases whereby dicotyledon seedlings can be grown efficiently in the infected soil to prevent related infection by dicotyledon diseases.

The process for biologically preventing dicotyledon diseases according to the present invention is based on the following.

The inventors have found that healthy interior tissues of a plant are in a pathogen-free state with some exceptions, the exceptions being a cyclamen, a sweet potato, a corn or a konjak (of a devil's-tongue).

In addition, we have found that a seed of any of these pathogen-containing plants is germ-free until a cotyledon opens after sprouting, and bacteria are forced into the interior tissues of the seed through its hypocotyl and trapped therein.

The present inventors have conceived of applying the aforementioned process for inoculating symbiotical bacteria having antifungal activity into the interior tissues of other plants.

The essential feature of this invention is as follows.

A seedling of dicotyledon is cut at a middle portion of its hypocotyl, and the cut seedlings are immersed into a symbiotical bacteria suspension having antifungal activity.

DETAILED DESCRIPTION OF THE INVENTION

Figure 1:
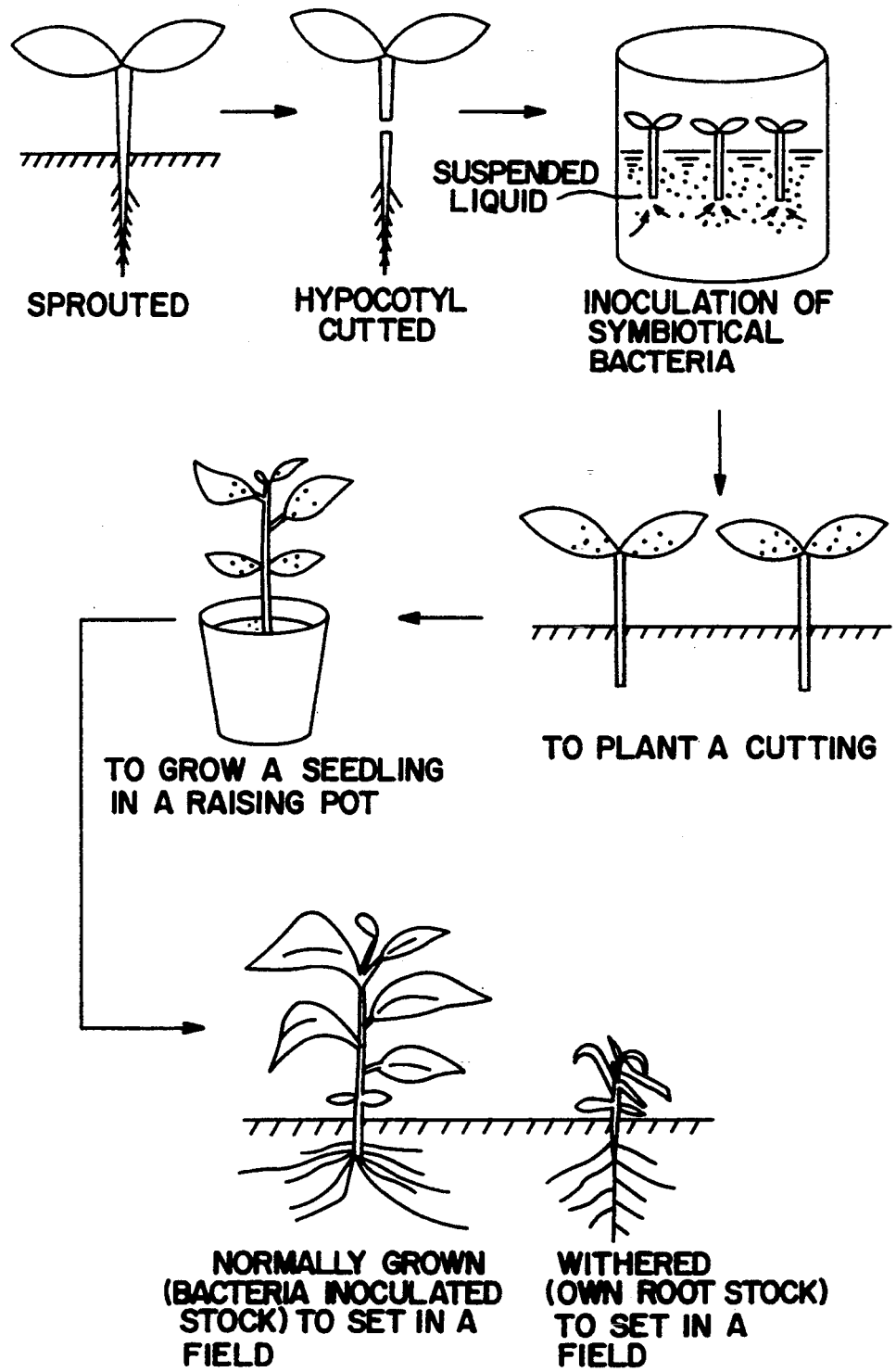
FIG. 1 illustrates symbolically the process of the invention.

More specifically, the present invention provides a process for biologically preventing dicotyledonous plant diseases which comprises:

cutting a seedling of a dicotyledon which includes the seedling between a cotyledon and less than three leaves at a growth stage;

immersing the upper portion of said cut seedling into a symbiotical bacteria suspension (preferably $10^4$ CFU/ml) having antifungal and antibacterial activities and induced resistance to plant pathogens in order to inoculate said symbiotical bacteria into interior tissues in the vessel and intercellular space of said dicotyledonous plants;

cutting said seedlings in a nursery bed or directly planting them in a field for further association of said symbiotical bacteria; and preventing said dicotyledonous plant diseases of said dicotyledonous plants.

The symbiotical bacteria preferably live symbiotically in non-symptomatic tissues of dicotyledonous plants such as cyclamen, sweet potato, strawberry, and monocotyledonous plants such as vuylstkeala, dendrobium, vanda, miltonia, cattleya and cymbidium, and the isolated bacteria preferably belong to Pseudomonas, Xanthomonas, Erwinia, Bacillus, *Streptomyces griseochoromoges* and Corynebacterium.

Preferably, the inoculum population of symbiotical bacteria is $10^4$ CFU/ml of the suspension. This population is used in the experiments described hereinafter. The upper portion of the cut seedlings is immersed in the suspension for 2–12 hours to inoculate the dicotyledonous plants.

The dicotyledon seedling is grown after being cut into the intended plant, and is transplanted in a desired pot and cultivated. Alternatively, the dicotyledon seedling is directly sowed into the infected field for cultivation.

The aforementioned symbiotical bacteria having antifungal activity are inoculated into the interior tissues of the dicotyledon and associated whereby dicotyledon diseases can be biologically controlled by antifungal activity and induced resistance.

The bacteria having antifungal activity on the dicotyledon diseases are those living symbiotically in non-symptomatic tissues of dicotyledonous plants such as cyclamen, sweet potato, strawberry and monocotyledonous plants such as vuylstkeala, dendrobium, vanda, miltonia, cattleya and cymbidium.

these isolated bacteria belong to Pseudomonas, Xanthomonas, Erwinia, Bacillus, *Streptomyces griseochromoges* and Corynebacterium.

These bacteria have been deposited with the Patent Bacteria Deposit Center which belongs to the Industrial Technical Institute of Microorganisms of the Government Agency of Industrial Science and Technology, Japan with various Bikohken-kin numbers Nos. FERM P-11625, FERM P-11626, FERM P-11627, FERM P-11628, and FERM P-11629, on Jul. 26, 1990; and Deposit Nos. FERM P-13742, FERM P-13743, FERM P-13744, FERM P-13745, FERM P-13746, FERM P-13747, FERM P-13748, FERM P-13749, and FERM P-13750 on Jul. 14, 1993.

EXAMPLES

Example 1

In order to carry out a process of this invention, various portions such as a lateral bud, a stem or a hypocotyl of a seedling of a tomato were cut, subsequently the cut portions were immersed into a symbiotical bacteria suspension for 12 hours to inoculate the symbiotical bacteria sufficiently, cut into other seedlings and were sowed in a raising pot.

The surface of the raised seedlings were sterilized in 70% ethanol for 1 minute, again sterilized in 0.001% concentration of mercury (11) chloride for 1 minute and ground in a 1% solution of peptone followed by streak out culture on a bouillon agar, and the colonies thus grown were reisolated to obtain the symbiotical bacteria from the tissues.

As shown in TABLE 1, the symbiotical bacteria could have been reisolated from the hypocotyl inoculated region at a high ratio, but they could not have been reisolated from the other regions.

A seedling of a tomato, whose cotyledon had opened after sprouting, was out at a middle portion of its hypocotyl (a seedling between sprouting of a cotyledon and after two leaves have grown). The cut seedlings were immersed into a suspended liquid containing the aforementioned reisolated symbiotical bacteria for 12 hours to inoculate the symbiotical bacteria.

The tomato seedlings thus treated were cut into other seedlings and seeded in a raising pot. The tomato seedlings were transplanted into a soil which had been infected with the aforementioned disease.

As shown in TABLE 2, it has been discovered that the tomato seedlings were cultivated efficiently, grown without being infected with plant diseases, and wilting had been biologically prevented.

Example 2

Various portions (lateral bud, stem or hypocotyl) of seedlings of a bottle gourd and of a cucumber were cut at their hypocotyls, and were immersed in a symbiotical bacteria suspension for 12 hours to inoculate the symbiotical bacteria.

These seedlings thus treated were cut into other seedlings and seeded in a raising pot. The seedlings were transplanted into a soil which was infected with the aforementioned disease.

The surfaces of the raised seedlings were sterilized in 70% ethanol for 1 minute, again sterilized in 0.001% concentration of mercury (11) chloride for 1 minute and ground in a 1% solution of peptone followed by streak out culture on a bouillon agar, and the colonies thus grown were reisolated to obtain the symbiotical bacteria from the tissues.

As shown in TABLES 3 and 4, the symbiotical bacteria could have been reisolated from the hypocotyl inoculated region at a high ratio, but they could not have been reisolated from the other regions.

Seedlings of a bottle gourd and of a cucumber (whose cotyledons have opened and two leaves have grown) were cut at their hypocotyls, and were immersed in a suspended liquid containing symbiotical bacteria for 12 hours to inoculate the symbiotical bacteria.

The seedlings were cut, seeded in a raising box, and subsequently transplanted into the infected soil.

As shown in TABLES 5 and 6, growth of the seedlings of the bottle gourd and of the cucumber has been improved without being infected with diseases, and stem rot has been biologically prevented.

Figure 2:
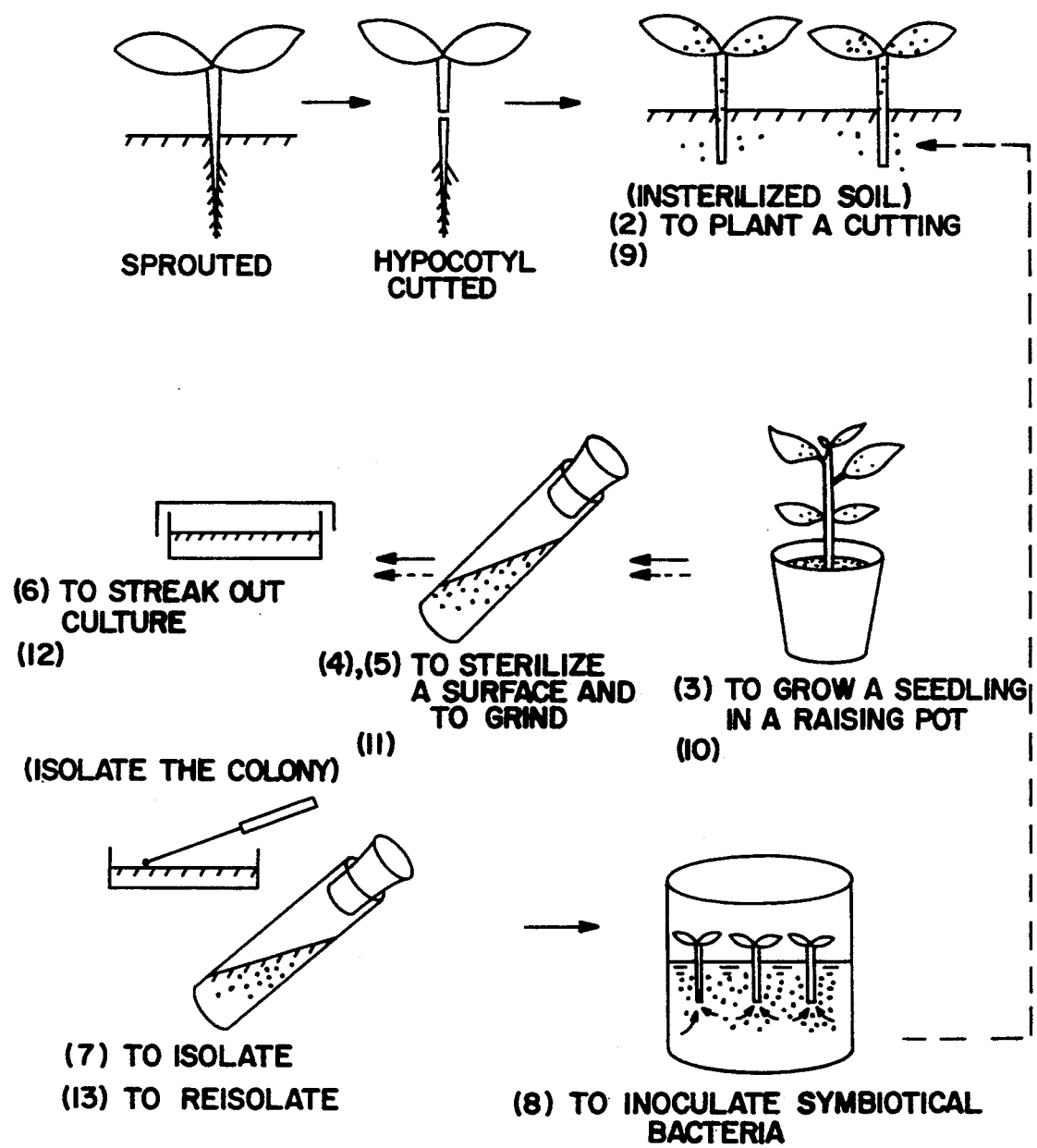
FIG. 2 illustrates the isolation of the bacteria in Example 2.

The isolation of symbiotical bacteria in Example 2 is described in the following and in FIG. 2.

(a) a hypocotyl of a seedling, whose cotyledon has opened after sprouting (and one to three leaves have grown), was cut at a middle portion thereof.

(b) The cut seedlings were cut in a non-sterilized soil to inoculate and also to trap symbiotical bacteria, dicotyledonous plants, within the tissues.

(c) The cut seedlings were sowed in a raising pot.

(d) The seedlings, having taken root, were collected, and the surfaces of the seedlings were sterilized in 70% ethanol for 1 minute, and sterilized again in 0.001% concentration of mercury (11) chloride.

(e) The seedlings were ground in a 1% solution of peptone.

(f) The ground solution was streak out cultured on a bouillon agar and a potato agar.

(g) The colony was cultured in a cryogenic room at 25° C. for about 1 week, and subsequently the colony thus grown was isolated.

(h) The cut seedlings of the dicotyledonous plants, whose hypocotyls have been cut, were immersed in a symbiotical bacteria suspension to inoculate the symbiotical bacteria, cut into other seedlings, and transplanted into a raising pot.

(i) Having checked the grown seedlings, the steps of the aforementioned (d), (e), (f) and (g) were repeated to reisolate the aforementioned symbiotical bacteria.

The isolated bacteria belong to Pseudomonas, Xanthomonas, Erwinia, Bacillus, *Streptomyces griseochoromoges* and Corynebacterium.

OTHER EXAMPLES

In addition, it has been found that the process of this invention has the excellent effects for biologically preventing Verticillium wilt of an eggplant belonging to Solanaceao (as shown in TABLE 7), Bacterial wilt of a pimento (as shown in TABLE 8), Fusarium wilt of a pumpkin and a melon (*Cucumis melo*) belonging to the Cucumbitae family (as shown in TABLES 9 and 10), Club-root of a Chinese cabbage, a cabbage and a broccoli belonging to Cruciferae (as shown in TABLES 11, 12 and 13), Verticillium wilt of a soybean and a kidney bean belonging to Leguminosae (as shown in TABLES 14 and 15), and Fusarium wilt of a spinach belonging to *Chenopodium album*.

EFFECT

As mentioned in the foregoing paragraphs, the process of this invention is characterized in that a seedling of a dicotyledon is cut at a middle portion of its hypocotyl, symbiotical bacteria having antifungal activity on plant diseases are inoculated into interior tissues thereof through the cut portions and associated, and the seedlings immersed with the symbiotical bacteria are either cut or seeded directly in a field whereby dicotyledon diseases can be biologically prevented.

Accordingly, the disadvantages of conventional methods for countering soil diseases can be substantially eliminated.

In other words, the conventional methods such as soil disinfection, cut cultivation, growing a new type of improved plant, inefficient and simple spreading of useful bacteria in the plant and soil, adsorption of the useful bacteria into the carriers ignoring the environment and ecosystem, and instability of plants having improved bacteria have been fully overcome.

At the same time, dicotyledons can be cultivated economically and efficiently, by using the natural morphosis of symbiotical bacteria in order to biologically prevent plant diseases.

The process of this invention can be advantageously used to cultivate a cell seedling and also to carry out short-term cultivation.

TABLE 1

Affinity of symbiotical bacteria to various portions of a tomato (Result of reisolation)

| inoculated portion | reisolated from | | |
|---|---|---|---|
| | hypocotyl | stem | lateral bud |
| lower hypocotyl | + | + | + |
| stem | − | − | − |
| lateral bud | − | − | − |

+: positive reaction.
−: negative reaction.
(same definitions for "+" and "−" apply hereinafter)

TABLE 2

Test results of biologically preventing wilt of a tomato by the process of this invention

| inoculated portion | days after transplantation | | |
|---|---|---|---|
| | 55 days | 73 days | 84 days |
| hypocotyl | — | — | — |
| stem | poor growth | wilt | withered |
| lateral bud | poor growth | wilt | withered |

TABLE 2-continued

Test results of biologically preventing wilt of a tomato by the process of this invention

| inoculated portion | days after transplantation | | |
|---|---|---|---|
| | 55 days | 73 days | 84 days |
| seed | poor growth | wilt | withered |
| own root | withered | withered | withered | poor growth: substantially less growth than in the present invention.
wilt: drooping.
withered: died.
(same definitions apply hereinafter)

TABLE 3

Affinity of symbiotical bacteria to various portions of a bottle gourd (Results of reisolation)

| inoculated portion | reisolated from | | |
|---|---|---|---|
| | hypocotyl | stem | lateral bud |
| hypocotyl | + | + | + |
| stem | − | − | − |
| lateral bud | − | − | − |

TABLE 4

Affinity of symbiotical bacteria to various portions of a cucumber (Results of reisolation)

| inoculated portion | reisolated from | | |
|---|---|---|---|
| | hypocotyl | stem | lateral bud |
| hypocotyl | + | + | + |
| stem | − | − | − |
| lateral bud | − | − | − |

TABLE 5

Test results of biologically preventing Fusarium wilt of a bottle gourd by the process of this invention

| inoculated portion | days after transplantation | | | |
|---|---|---|---|---|
| | 31 days | 40 days | 60 days | 90 days |
| hypocotyl | — | — | — | — |
| seed | — | — | — | wilt |
| not inoculated | poor growth | wilt | wilt | wilt |
| own root | withered | withered | withered | withered |

TABLE 6

Test results of biologically preventing Fusarium wilt of a cucumber by the process of this invention.

| inoculated portion | days after transplantation | | | |
|---|---|---|---|---|
| | 31 days | 40 days | 60 days | 90 days |
| hypocotyl | — | — | — | — |
| seed | — | — | — | wilt |
| not inoculated | poor growth | wilt | withered | withered |
| own root | withered | withered | withered | withered |

TABLE 7

Test results of biologically preventing Verticillium wilt of an eggplant by the process of this invention

| inoculated portion | days after transplantation | | |
|---|---|---|---|
| | 55 days | 73 days | 84 days |
| hypocotyl | — | — | — |
| stem | poor growth | wilt | withered |
| lateral bud | poor growth | wilt | withered |
| seed | poor growth | wilt | wilt |
| own root | wilt | withered | withered |

TABLE 8

Test results of biologically preventing Bacterial wilt of a pimento by the process of this invention

| inoculated portion | days after transplantation | | |
|---|---|---|---|
| | 10 days | 20 days | 30 days |
| hypocotyl | — | — | — |
| stem | poor growth | wilt | withered |
| seed | poor growth | wilt | withered |
| own root | poor growth | withered | withered |

TABLE 9

Test results of biologically preventing Fusarium wilt of a pumpkin by the process of this invention

| inoculated portion | days after transplantation | | | |
|---|---|---|---|---|
| | 31 days | 40 days | 60 days | 90 days |
| hypocotyl | — | — | — | — |
| seed | — | poor growth | wilt | withered |
| own root | wilt | withered | withered | withered |
| not inoculated | poor growth | wilt | withered | withered |

TABLE 10

Test results of biologically preventing Fusarium wilt of a melon by the process of this invention

| inoculated portion | days after transplantation | | | |
|---|---|---|---|---|
| | 31 days | 40 days | 60 days | 90 days |
| hypocotyl | — | — | — | — |
| seed | — | — | wilt | wilt |
| not inoculated | poor growth | wilt | withered | withered |
| own root | withered | withered | withered | withered |

TABLE 11

Test results of biologically preventing Club-root of a Chinese cabbage by the process of this invention

| inoculated portion | reisolated | degree of disease | weight of crop |
|---|---|---|---|
| hypocotyl | + | 1.7 | 237 |
| not inoculated | + | 3.3 | 136 |
| own root | — | 2.6 | 217 |

For "degree of disease":
0: no symptom.
1: faintly infected.
2: weakly infected.
3: typically infected.
4: severely infected.
5: withered (died).
(same definitions apply hereinafter)

TABLE 12

Test results of biologically preventing Club-root of a cabbage by the process of this invention

| inoculated portion | reisolated | degree of disease | weight of crop |
|---|---|---|---|
| hypocotyl | + | 0.6 | 203 |
| not inoculated | + | 3.0 | 155 |
| own root | — | 2.9 | 196 |

TABLE 13

Test results of biologically preventing Club-root of a broccoli by the process of this invention

| inoculated portion | reisolated | degree of disease | weight of crop |
|---|---|---|---|
| hypocotyl | + | 0.6 | 203 |
| not inoculated | + | 3.0 | 155 |
| own root | — | 2.9 | 196 |

TABLE 14

Test results of biologically preventing Verticillium wilt of a beam by the process of this invention

| inoculated portion | reisolated | degree of disease |
|---|---|---|
| hypocotyl | + | — |
| upper hypocotyl | + | — |
| not inoculated | + | wilt |
| own root | — | withered |

TABLE 15

Test results of biologically preventing Verticillium wilt of a kidney bean by the process of this invention

| inoculated portion | reisolated | degree of disease |
|---|---|---|
| hypocotyl | + | — |
| upper hypocotyl | + | — |
| not inoculated | + | wilt |
| own root | — | withered |

TABLE 16

Test results of biologically preventing Fusarium wilt of a spinach bean by the process of this invention

| inoculated portion | reisolated | degree of disease |
|---|---|---|
| hypocotyl | + | — |
| not inoculated | + | — |
| own root | — | withered |

TABLE 17

Affinity of symbiotical bacteria trapped within the plant tissues and their affinity within the plant tissues

| family | gene | number of trapped bacteria (CPU/g) | Affinity |
|---|---|---|---|
| Solanaceae | tomato (*Locopersicon esclentum*) | 6540 | + |
| | eggplant (Melongena) | 760 | + |
| | pimento (*Capsicum annuum*) | 2120 | + |
| | Guinea pepper (*Capsicum annuum*) | 3050 | + |
| Cucurbitaceae | bottle gourd (*Laegenaria siceraria*) | 3460 | + |

TABLE 17-continued

Affinity of symbiotical bacteria trapped within the plant tissues and their affinity within the plant tissues

| family | gene | number of trapped bacteria (CPU/g) | Affinity |
|---|---|---|---|
| | cucumber (*Cucumis sativus*) | 7860 | + |
| | melon (*Cucumis melo* var. inodorus) | 5320 | + |
| | muskmelon (*Cucumis melo* var. reticulatus) | 6040 | + |
| | oriental pickling (*Cucumis melo* var. conomon) | 3430 | + |
| | oriental melon (*Cucumis melo* var. acidulus) | 9860 | + |
| | balsam pear (*Momordica charantia*) | 1682 | + |
| | sponge gourd (*Luffa cylindrica*) | 5650 | + |
| | watermelon (*Citrulius lanatus*) | 4392 | + |
| | pumpkin (*Cucurbita ficifolia*) | 8789 | + |
| Cruciferae | Chinese cabbage (*Brassica campestria* var. pekinensis) | 4880 | + |
| | broccoli (*Brassica campestria*) | 3520 | + |
| | radish (*Raphanus sativus* var. longipinnatus) | 2960 | + |
| | tunip (*Brassica campestris* var. rapa) | 164 | + |
| Leguminosae | soybean (*Glycine max*) | 7400 | |
| | kidney bean (*Phaseolus angularis*) (*Spinacia oleracen*) | 5724 | + |
| | watermelon (*Citrulius lanatus*) | 4392 | + |
| | pumpkin (*Cucurbita ficifolia*) | 8789 | + |
| Cruciferae | Chinese cabage (*Brassica campestria* var. pekinensis) | 4880 | + |
| | broccoli (*Brassica oleacea* var. italica) | 3520 | + |
| | radish (*Raphanus sativus* var. longipinnatus) | 2960 | |
| | turnip (*Brassica campestris* var. rapa) | 164 | |
| Leguminosae | soybean (*Glycine max*) | 7400 | + |
| | kidney beaen (*Phaseolus vulgaris*) | 5724 | + |
| | azuki bean (*Phaseolus angularis*) | 194 | |
| Chenopodiaceae | spinach (*Spinacia oleracen*) | 430 | + |
| Umbelliferae | carrot (*Daucus carota*) | 180 | + |
| Ranunculaceae | delphinium (*Delphinium ajacis*) | | |
| Rosaceae | strawberry (*Fragaria x ananassa*) | 230 | + |
| Malvaceae | gumbo (*Abelmoschus osculentus*) | 1420 | + |
| Polygonaceae | buckwheat (*Pagopyrum esculentum*) | 2400 | + |
| | Chinese indigo (*Percicaria tinctoria*) | 6920 | + |

TABLE 17-continued

| | Affinity of symbiotical bacteria trapped within the plant tissues and their affinity within the plant tissues | | |
|---|---|---|---|
| family | gene | number of trapped bacteria (CPU/g) | Affinity |
| Compotitae | lettuce (*Lactuca sativa*) | 7090 | + |
| | safflower (*Carthamus tinctorius*) | 644 | + |

While in the foregoing specification, embodiments of the invention have been set forth in considerable detail for the purpose of making a complete disclosure of the invention, it will be apparent to those of ordinarily skill in the art that numerous changes may be made in such details without departing from the spirit and principles of the invention.

What is claimed is:

1. A process for biologically preventing dicotyledonous plant diseases which comprises:
   (a) cutting a seedling of a dicotyledon, at a growth stage between a cotyledon and less than three leaves, at the middle of the dicotyledon;
   (b) immersing the cut seedling into a symbiotical bacteria suspension having antifungal and antibacterial activities and resistance to plant pathogens in order to inoculate said symbiotical bacteria into interior tissue vessels and intercellular spaces of said dicotyledonous plants; and
   (c) cutting seedling into a nursery bed or directly planting it in a field.

2. The process for biologically preventing dicotyledonous plant diseases as claimed in claim 1, wherein said symbiotical bacteria are obtained from asymptomatic tissues of dicotyledonous plants selected from the group consisting of cyclamen, sweet potato, and strawberry, or monocotyledonous plants selected from the group consisting of vuylstkeala, dendrobium, vanda, miltonia, cattleya and cymbidium, and wherein the symbiotical bacteria are selected from the group consisting of Pseudomonas, Xanthomonas, Erwinia, Bacillus, *Streptomyces griseochoromoges* and Corynebacterium.

* * * * *

UNITED STATES PATENT AND TRADEMARK OFFICE
CERTIFICATE OF CORRECTION

PATENT NO. : 5,401,655
DATED : March 28, 1995
INVENTOR(S) : Toshio Kijuma, et. al.

It is certified that error appears in the above-indentified patent and that said Letters Patent is hereby corrected as shown below:

```
Title page, item [30] add the followings: Under Foreign Application
Priority Data..........Sept. 10, 1991 [JP]  .........259914/1991--.
```

Signed and Sealed this

First Day of August, 1995

Attest:

BRUCE LEHMAN

*Attesting Officer*   *Commissioner of Patents and Trademarks*